United States Patent [19]

Castillo

[11] Patent Number: 4,599,998
[45] Date of Patent: Jul. 15, 1986

[54] ADJUSTABLE POLYCENTRIC ORTHOPEDIC APPLIANCE HINGE

[76] Inventor: James D. Castillo, 22671 Via Santiago, Mission Viejo, Calif. 92691

[21] Appl. No.: 616,059

[22] Filed: Jun. 1, 1984

[51] Int. Cl.$^4$ ............................................. A61F 3/00
[52] U.S. Cl. .................................. 128/77; 128/80 C; 128/80 F; 74/109; 74/526; 403/62; 403/84
[58] Field of Search ............... 128/80 C, 80 F, 80 R, 128/88, 77; 3/22, 12.2, 12.3; 403/62, 84; 74/109, 104, 526

[56] References Cited

U.S. PATENT DOCUMENTS

| 304,696 | 9/1884 | Bronson | 3/22 X |
| 505,382 | 9/1893 | Berghoff | 128/88 |
| 552,143 | 12/1895 | Rankin | 128/88 |
| 1,330,298 | 2/1920 | Baird | 74/526 X |
| 4,370,977 | 2/1983 | Mauldin et al. | 128/80 F |
| 4,372,298 | 2/1983 | Lerman | 128/80 C |
| 4,381,768 | 5/1983 | Erichsen et al. | 128/80 C |
| 4,520,802 | 6/1985 | Mercer et al. | 128/80 C |
| 4,520,804 | 6/1985 | DiGeorge | 128/80 C |
| 4,524,764 | 6/1985 | Miller et al. | 128/80 C |

FOREIGN PATENT DOCUMENTS

| 26961 | of 1906 | United Kingdom | 403/62 |
| 464686 | 4/1937 | United Kingdom | 74/526 |

Primary Examiner—Clifford D. Crowder
Attorney, Agent, or Firm—Grover A. Frater

[57] ABSTRACT

An orthopedic hinge is polycentric and employs a rack cooperating with pinions formed at the ends of the hinge arms. A special arrangement for limiting rack displacement is effective to selectively clamp the hinge arms at a given arm angle or to permit movement within a limited range of allowable angles.

17 Claims, 6 Drawing Figures

U.S. Patent    Jul. 15, 1986    4,599,998
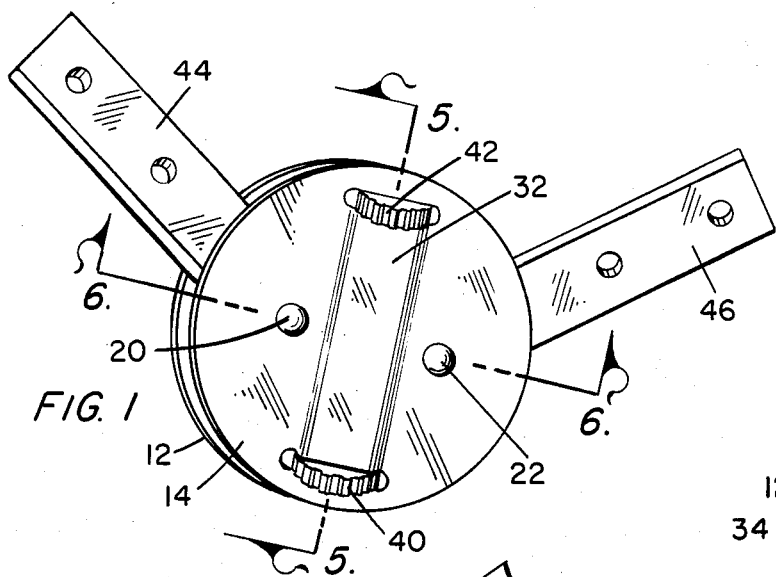
FIG. 1
FIG. 2
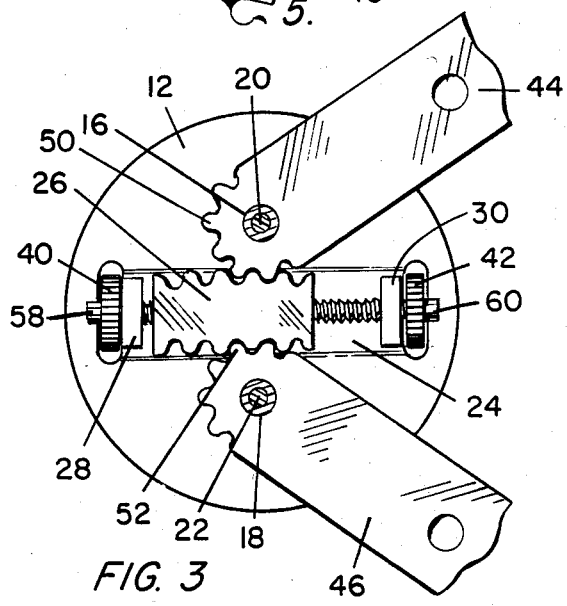
FIG. 3
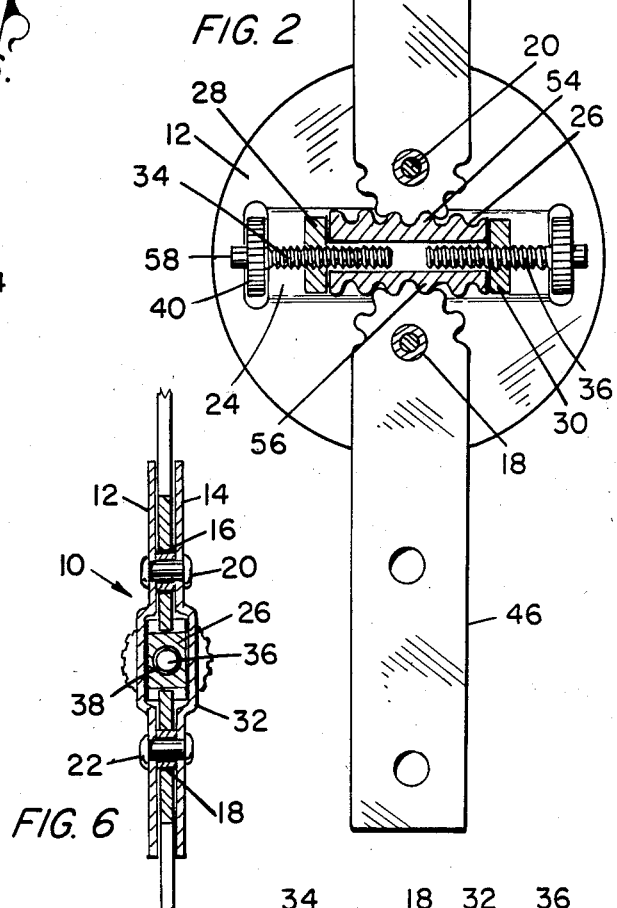
FIG. 6
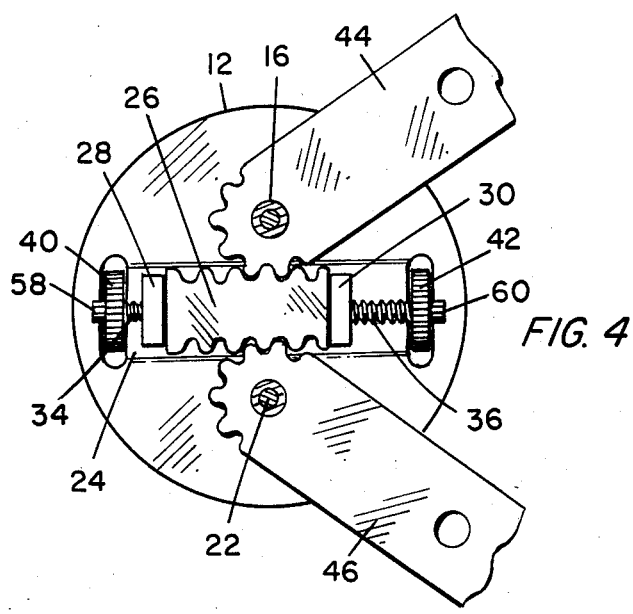
FIG. 4
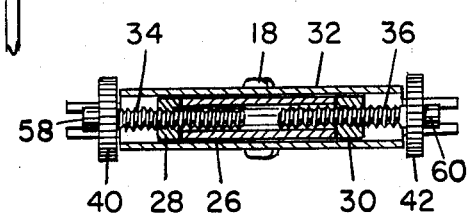
FIG. 5

ADJUSTABLE POLYCENTRIC ORTHOPEDIC APPLIANCE HINGE

TECHNICAL FIELD

This invention relates to improvements in hinges, and it relates in particular to hinges for use in orthopedic appliances.

BACKGROUND ART

While hinges of the kind that are provided by the invention are not limited to use in orthopedic appliances, they are particularly useful in that connection. It is not uncommon for physicians to prescribe the use of an appliance which includes a means for holding limbs bent at a selected angle at the elbow or wrist or knee. If bending is permitted, the bending may be limited not only in degree but to some particular portion in the range of angular movement. In many instances the physician prescribes that the degree of bending is to be altered with time.

In those cases the appliance is a two-part cast or brace. One part is fixed to the limb below the joint and the other above. The two parts or sections are interconnected with a hinge. Some means is provided for locking the hinge elements at a selected angular degree of hinge opening. While in some prior art designs that angle may be changed by unlocking and relocking the hinge, the degree of change is limited. Hinges that limit angular movement over any segment of a wide range of angles have not been available.

Bending movement at knees and elbows and wrists does not occur about a single pivot point. Cast sections that are joined by a single pivot hinge, with the limb bent at a particular angle, may permit small change in the angle between the cast sections when the pivot axis of the hinge, and of the elbow or knee, are coincident, or nearly so. But when bending of the joint proceeds to a point at which the pivot axes of hinge and joint are no longer aligned, the cast or brace applies forces to limb and joint that can be both intolerably uncomfortable and injurious. In that case the single pivot hinge is entirely inadequate.

DISCLOSURE OF INVENTION

It is an object of the invention to provide an improved, limited action hinge, and a particular object to provide an improved hinge for use as an element of an orthopedic appliance.

Another object is to provide an improved polycentric hinge that can simulate in relatively close degree the hinge action that occurs at human elbows and knees.

A further object is to provide a hinge which will permit a selected degree of hinge action over any selected segment of a wide range of angular hinge actions.

Another object is to provide for easy change in the adjustment of such a hinge to the end that adjustment may be made to an orthopedic appliance in which it is incorporated readily and without need to modify the appliance.

These and other objects and advantages of the invention, which will be apparent upon examination of the specification and accompanying drawings, are realized in part by the provision of a hinge the hinge arms of which are pivotal about space axes and which arms are engaged with one another and with a drive member such that the rotational position of the arms, and thus the angle between them, is altered, one clockwise and the other counterclockwise, about their respective pivot axes upon translation of the drive member relative to said pivot axes along some line of movement. Those elements are combined with a stop that limits the degree of such translation of the drive member in at least one direction and, in the preferred form, in both directions.

In the preferred forms of the invention the stop structures for defining the end limits of arm rotation are separate, one for each end limit, and they are independently adjustable. Accordingly, both the angular movement that is permitted and the segment of the range of movements in which such angular movement is permitted may be adjusted. The preferred form permits angular rotation of the lever arms from full range to prevention of any movement from a given angular position within the range.

BRIEF DESCRIPTION OF THE DRAWINGS

FIG. 1 is an isometric view of a preferred form of a polycentric hinge according to the invention;

FIG. 2 is a cross-sectional view taken on a plane along the surface of the lever arms parallel to the center plane of lever movement;

FIG. 3 is a cross-sectional view taken on a plane that includes the surface of the drive member, the upper base plate having been removed and the lever and stop elements having a condition different from their condition in FIG. 2;

FIG. 4 is a view corresponding to FIG. 3 except that the stops are shown in different condition;

FIG. 5 is a cross-sectional view taken on line 5—5 of FIG. 1; and

FIG. 6 is a cross-sectional view taken on line 6—6 of FIG. 1.

DESCRIPTION OF THE PREFERRED EMBODIMENT

The six figures of the drawing all relate to and depict what is the preferred form of the invention. It is intended for applications in which it is, or may be, desirable to permit limited bending of a knee or elbow or wrist. Subsets and readily understood modifications of the form shown may be preferred for certain applications such, for example, as applications in which no bending movement of the joint is to be permitted except that the degree of joint bending is to be changed from time to time. Some of the possible variations of the design will be explained below following description of the illustrated embodiment.

The primary elements in this design are a member to serve as a base; two lever arms which are pivotally mounted at spaced, respectively associated axes and which may be as long or as short as desired and which may have a variety of shapes and which need not look alike; a drive member which is moveable relative to either or both of the base and one of the lever pivot axes; and a means which may have a variety of forms by which to limit movement of the drive member so that it cannot move or, if permitted to move, so that movement is limited in selected degree.

The unit 10 shown in FIGS. 1 through 6 is symmetrical about the vertical center plane through FIG. 6. Either of the two side plates 12 and 14 may be considered to be a base and the other a cover plate. For the purpose of this description plate 12 is designed the base, and plate 14 is the cover. They are circular in this embodiment and are held in spaced parallel planes by the combination of two cylindrical spacers 16 and 18 which hold them apart, and two rivets 20 and 22 which hold the assembly together.

The central region of the base and cover are offset from the remainder of those elements to form a generally rectangular inner depression in each of them between the two spacers. The depression in each case is shaped symmetrically about a center line between the spacers and the line connecting the axes of the two spacers. The inverse of the depressions are outer bulges. The bulge 32 of cover 14 is best seen in FIG. 1. Both are visible in FIGS. 5 and 6. The depression in the base is designated 24 and may be seen in FIGS. 2, 3 and 4. The degree of offset is not critical. Its purpose is to form a slot to contain a drive member 26 and a pair of stop elements 28 and 30 and to confine those stop elements and drive member to movement along a line of action peprpendicular to a line connecting the two rivets. The fact that the stop elements and drive member are thicker than the spacers 16 and 18 are long is best shown in FIGS. 5 and 6.

The drive member 26 is free to move back and forth in the channel formed by the two depressions except as that movement is limited by engagement with the stop elements. Those elements are threadedly engaged on respectively associated lead screws. Element 28 is threaded on lead screw 34 and element 30 is threaded on lead screw 36. The lead screws are aligned on a common axis and their inner ends extend into a bore 38 of the drive member 26. The bore 38 is formed on the same common axis with the lead screws, and in this version of the product the diameter, diameter of bore 38, exceeds the outer diameter of the lead screws. That may be seen in FIG. 6. The lead screws impose no limitation on movement of the drive member except to the extent that they drive the stop elements to positions in which the stop elements limit drive element translation.

Each lead screw is fixed to and rotatable with a respectively associated thumb wheel. The thumb wheels have a diameter greater than the thickness of the base and cover plate combination. They extend through slots formed in the cover and base at the ends of the rectangular depressions. As a consequence, the thumb wheels, and therefor the lead screws, are restrained against displacement along the lead screw axis. Instead, the lead screws are limited to rotational motion and it is the stop elements that are displaced. For identification, lead screws 34 and 36 are fixed to thumb wheels 40 and 42, respectively.

The drive screws rotate independently. Accordingly, the stop members 28 and 30 are positioned independently. If they are positioned each flush with its associated end of the drive member 26, the drive member will be held aainst translation. That condition is depicted in FIGS. 4, 5 and 6. In FIGS. 5 and 6 the drive member is fixed midway along its range of displacement along its line of travel or action. In FIG. 4 the drive member is held fixed near the left most limit of its range of displacement.

In FIG. 3 the stop elements are retracted back to their respective thumb wheels. As a consequence, the drive member 26 is allowed its full range of displacement between the two stop elements. Displacement can be limited to one segment of that full range by rotation of their respective thumb wheels to drive one or both of the stop elements 28 and 30 to the positions that are to mark the left and right limits of drive element displacement, respectively.

It is the function of the drive element to change the relative angular orientation of the lever arms of the hinge when the drive element is translated along its line of action and to hold the lever arms against change in angular displacement when the drive element is held against translation.

In the event that the stop elements are separated sufficiently to permit drive element movement, it is a function of the dirve element to move and change its position whenever an external force, such as the bending of an elbow or knee, is applied to force relative movement between the lever arms to change the angle between them.

The hinge arms in this case are bored near one end to receive a respectively associated one of the two spacers 16 and 18. The arms are mounted on the spacers for rotation about the axis of the spacers and the rivets 20 and 22. Arm 44 is mounted on spacer 16 and arm 46 is mounted on spacer 18. It is to these arms that the orthopedic cast or brace structure is fixed or connected, and the outer sections of the arms may have almost any shape to facilitate that purpose. The inner ends, however, must have a connection to the drive member either directly, as shown, or indirectly so that translation of the drive member rotates both of the arms relative to the base. The connection need not be direct. It could, for example, be made through idler gears.

In this preferred example, each side of the drive member toward one of the hinge arms is formed with a series of teeth along its edge. Those teeth mesh with teeth formed around the periphery of the semi-circular inner end of a respectively associated one of the hinge arms. In the case of each arm the drive member has the form of a rack, and the end of the arm serves as a pinion. For identification, one of the teeth on arm 44 is numbered 50 and one of those on arm 46 is numbered 52 (FIG. 3). One of the teeth of the drive "rack" 26 that engages the teeth of arm 44 is numbered 54 and one that engages the teeth of arm 46 is numbered 56 (FIG. 2).

That both arms move is important so that the pivot point of the hinge follows the pivot point of the elbow or knee or wrist. The pivot point of the hinge moves as the hinge angle is changed. That movement does not reproduce the hinge action at either elbow or knee exactly, but it can match that action rather closely in the case of both knee and elbow if the spacing between the pivot axes of the two levers is correct. For most adults a spacing of two and one-half to three centimeters is correct. The hinge action matches wrist action less closely but well enough to be useful in wrist appliances without change in the spacing between the rotational axes of the hinge arms.

In many applications it is desired that the appliance wearer not be permitted to alter some fixed degree of bending of his/her arm or leg, but it is desired that the cast or appliance be hinged to permit periodic change in the fixed hinge angle. In that case a hinge is required, and a polycentric hinge is preferred but it is not essential. It is sufficient in that case if the stop members are omitted and the drive member be threadedly engaged with the lead screw. Alternatively, one of the stop members may be bonded to the drive member to provide the same result.

No specific cast or brace is shown because of the wide variety of such appliances with which the invention is useful and because the cast or brace, per se, forms no part of the invention. The manner of attachment of hinges to orthopedic appliances is well known to orthopedic surgeons and orthopedic apparatus makers and needs no explanation here.

The thumb wheels have proven to be an easily used structure for making adjustments. The physician's order concerning the angle to which the hinge is to be adjusted and the degree of bending freedom the patient is to be given is carried out easily with the those thumb wheels. However, their very accessibility gives rise to the possibility of accidental turning. It is preferred to provide some impediment to such an occurrence. In this preferred form both thumb wheels include a small diameter extension on the side way from the lead screw. They can be seen in FIGS. 2 through 5 of the drawing in this case. The one associated with thumb wheel 40 is numbered 58. The other is numbered 60. Those extensions have a diameter greater than the height of spacers 16 and 18. The inner face of the base 12 and cover 14 is milled to form a groove in which the extension is disposed. That is best shown in FIG. 5. The milled groove is only deep enough to receive the extension with an interference fit. Friction at the interface of the extensions and the front and back plate 12 and 14 holds the thumb wheel against accidental rotation.

Although I have shown and described a specific embodiment of my invention, I am fully aware that many modifications thereof, and other embodiments, are possible. My invention, therefore, is not to be restricted except insofar as is necessitated by the prior art.

I claim:

1. In an adjustable hinge:
a base;
first and second hinge arms pivotally mounted at respectively associated first and second spaced points on said base;
a driven member moveable relative to said base and to both of said hinge arms and having driving connection to each of said hinge arms, said driven member being translated and each arm being rotated about its respective pivot in one direction through said driven member as an incident to application of force to one of said arms to cause translation of said driven member to drive the other of said hinge arms in the direction of rotation opposite to said one direction of rotation; and
stop means for imposing a limit on the translation of said driven member relative to said base in at least one direction whereby change in at least one direction of the rotational position of said hinge arms is limited relative to the base.

2. The invention defined in claim 1 in which said driven member is a toothed rack and in which said hinge arms are formed with teeth which are engaged with the teeth of the rack.

3. The invention defined in claim 1 in which said stop means is adjustable to change the positional limit of the driven member and arms relative to said base.

4. The invention defined in claim 3 in which said stop means is effective to impose a limit on the change in position of said driven member relative to said base.

5. The invention defined in claim 4 in which said stop means comprises a pair of stops each effective to limit the movement of said driven member to a given position relative to said base whereby said driven member is limited to movement between said positions.

6. The invention defined in claim 4 in which said stop means comprises a pair of stops each of which is moveable relative to the base independently of the other whereby the range and degree of movement of said driven member relative to said base is adjustable.

7. The invention defined in claim 4 in which said stop means is adjustable to fix the position of said driven member and said pivot arms to a selected one position in a range of positions relative to said base.

8. The invention defined in claim 1 in which said pivot arms are rotatable in a plane about spaced, parallel axes and in which said driven member is moveable in said plane along a line of movement between said axes whereby to effect rotational displacement of said lever arms.

9. The invention defined in claim 8 in which said stop means comprises a drive screw rotatable about its axis and fixed against longitudinal displacement relative to said base.

10. The invention defined in claim 9 in which said stop means further comprises a stop element threadedly engaged on said drive screw and translatable along said line of movement as an incident to rotation of said drive screw.

11. The invention defined in claim 8 in which said stop means comprises:
a pair of drive screws each rotatable about its axis and each fixed against longitudinal displacement relative to said base; and
means for limiting displacement of said driven means along its line of movement as a function of the degree of rotation of said drive screws.

12. The invention defined in claim 8 in which said driven means comprises a toothed rack and in which said hinge arms are formed with teeth which teeth are engaged in the teeth of the rack.

13. A polycentric orthopedic appliance hinge comprising a pair of hinge arms each capable of angular displacement over a range of angular displacements about a respectively associated pivot axis;
displacement means in the form of a driven member interposed between and connected to said hinge arms such that it is translated as a consequence of angular displacement of either one of said arms for forcing angular displacement of the other of said arms and such that the angle between the directions of said arms increases or decreases as the sum of their angular displacements; and
stop means in the form of means for limiting displacement of said displaceable driven member for limiting displacement of said arms to a selected segment of said range of angular displacements.

14. The invention defined in claim 13 in which said stop means is effective to selectively prevent change in the angle between the directions of said arms.

15. The invention defined in claim 13 in which said stop means comprises two stops independently adjustable, one effective to limit the maximum value of said angle and the other effective to limit the minimum value of the angle.

16. The invention defined in claim 15 in which said hinge arms are formed with teeth and in which said driven member is formed with teeth, the teeth of the driven member meshing with the teeth of at least one of said arms.

17. The invention defined in claim 16 in which said driven member is a rack and in which the teeth of the arms serve as pinions enmeshed with the teeth of the rack.

* * * * *